(12) United States Patent
Rogers

(10) Patent No.: US 7,597,699 B2
(45) Date of Patent: Oct. 6, 2009

(54) MOTORIZED SURGICAL HANDPIECE

(76) Inventor: William G. Rogers, 7508 Davenport La., Ocean Springs, MS (US) 39564

( * ) Notice: Subject to any disclaimer, the term of this patent is extended or adjusted under 35 U.S.C. 154(b) by 1010 days.

(21) Appl. No.: 11/188,390

(22) Filed: Jul. 25, 2005

(65) Prior Publication Data

US 2007/0021752 A1   Jan. 25, 2007

(51) Int. Cl.
*A61B 17/32*   (2006.01)

(52) U.S. Cl. .................. 606/180; 173/217; 277/412

(58) Field of Classification Search .............. 606/79, 606/80, 167, 180; 173/216, 217, 218; 277/412, 277/419
See application file for complete search history.

(56) References Cited

U.S. PATENT DOCUMENTS

| | | | |
|---|---|---|---|
| 2,144,342 A | 1/1939 | Morrison | |
| 3,049,018 A | 8/1962 | Lusskin et al | |
| 3,082,009 A | 3/1963 | Whitley et al | |
| 3,120,845 A | 2/1964 | Horner | |
| 3,302,951 A | 2/1967 | Olesen | |
| 3,324,552 A * | 6/1967 | Saffir | 433/82 |
| 3,347,604 A * | 10/1967 | Lavelle et al. | 384/134 |
| 3,804,423 A | 4/1974 | Booy | |
| 4,108,182 A | 8/1978 | Hartman et al. | |
| 4,203,222 A | 5/1980 | Mattchen | |
| 4,565,378 A | 1/1986 | Wehrfritz et al. | |
| 4,736,742 A | 4/1988 | Alexson et al. | |
| 4,802,852 A | 2/1989 | Shea | |
| 4,811,736 A | 3/1989 | Griggs et al. | |
| 4,913,447 A | 4/1990 | Jostlein | |
| 5,176,628 A | 1/1993 | Charles et al. | |
| 5,207,697 A | 5/1993 | Carusillo et al. | |
| 5,405,348 A | 4/1995 | Anspach, Jr. et al. | |
| 5,540,447 A | 7/1996 | Shultz et al. | |
| 5,779,474 A * | 7/1998 | Gonser | 433/129 |
| 5,794,942 A | 8/1998 | Vance et al. | |
| 6,007,556 A | 12/1999 | Kablik et al. | |
| 6,132,448 A | 10/2000 | Perez et al. | |
| 6,238,400 B1 | 5/2001 | Bays | |
| 6,293,957 B1 | 9/2001 | Peters et al. | |
| 6,565,587 B1 | 5/2003 | Heckele et al. | |
| 6,733,218 B2 | 5/2004 | Del rio et al. | |
| 2004/0059363 A1 | 3/2004 | Alvarez et al. | |
| 2004/0119238 A1* | 6/2004 | Skumawitz et al. | 277/412 |
| 2004/0211575 A1* | 10/2004 | Soika et al. | 173/48 |
| 2009/0131940 A1* | 5/2009 | Brunnett et al. | 606/80 |

* cited by examiner

*Primary Examiner*—Anhtuan T Nguyen
*Assistant Examiner*—Thomas McEvoy

(57) ABSTRACT

A motorized surgical handpiece comprises a housing enclosing an interior containing a motor and an output shaft for being driven in rotation by the motor. The output shaft has a central longitudinal axis, a bore extending therethrough for receiving a shank of a surgical tool to be rotatably driven by the output shaft, a forward end portion extending forwardly beyond the motor and a rearward end portion extending rearwardly beyond the motor. The housing has a continuous lumen extending entirely therethrough formed in part by the output shaft bore for insertion of a bore brush through the lumen for cleaning when the surgical tool is removed from the handpiece. The handpiece has forward and rearward labyrinth seals comprising rotor components respectively attached to the forward and rearward end portions of the output shaft for rotation in corresponding stator components with there being a labyrinthine clearance between each rotor component and its stator component to receive pressurized air during use and during cleaning of the handpiece to avoid the entry of contaminants.

20 Claims, 10 Drawing Sheets

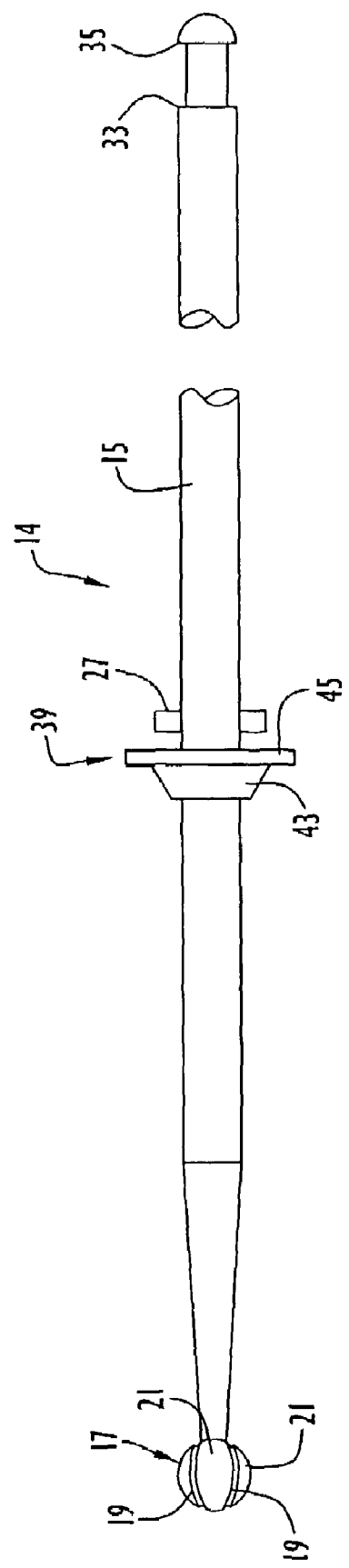

MOTORIZED SURGICAL HANDPIECE

BACKGROUND OF THE INVENTION

1. Field of the Invention

The present invention relates generally to motorized surgical handpieces including pressurized labyrinth seals and a hollow, motor driven rotatable output shaft with a through bore for receiving a shank of a surgical tool in driving engagement.

2. Brief Discussion of the Related Art

Motorized surgical handpieces are commonly used to rotatably drive surgical tools, such as drills and burs, to perform a cutting operation on anatomical tissue at a surgical site. Motorized surgical handpieces typically include a motor contained in the interior of a housing of the handpiece and an output shaft driven by the motor in rotation for being coupled to a shank of a surgical tool in driving engagement. The surgical tool typically includes the shank and a cutter carried by the shank to perform a cutting operation on anatomical tissue when the shank is rotatably driven by the output shaft. Depending on the cutting operation to be performed and the type of anatomical tissue to be cut with the cutter, it is oftentimes necessary for the output shaft to rotate the surgical tool at considerably high speeds. As a result of the cutting operation, debris including fluid and anatomical tissue is normally generated at the surgical site.

It is advantageous for the surgical tool to be removably or releasably coupled with the output shaft so that various different types of surgical tools can be selectively coupled with the output shaft interchangeably. In many motorized surgical handpieces, the output shaft is solid and the handpiece includes a separate coupling, such as a chuck, attached to the output shaft for releasably holding the shank of the tool in a cavity of the coupling to establish driving engagement between the output shaft and the surgical tool. The output shaft is not in direct driving engagement with the surgical tool but, rather, is indirectly engaged with the surgical tool via the intermediary of the separate coupling. Since the output shaft is solid, the cavity terminates at a blind end within the coupling.

Motorized surgical handpieces that have a solid output shaft and a separate coupling on the output shaft for receiving a shank of the surgical tool in a cavity of the coupling are particularly susceptible to problems arising from the entry of debris into the coupling. During the cutting operation, debris may travel along the shank of the surgical tool toward the coupling and may enter the cavity of the coupling around the shank of the surgical tool. The blind end of the cavity within the coupling undesirably promotes the accumulation of debris in the coupling. A conventional approach to cleaning the coupling of debris involves removing the shank of the surgical tool from the cavity, pushing a bore brush into the vacated cavity, and withdrawing the bore brush from the cavity in hope that most of the debris will have attached itself to the bristles of the brush and will be removed from the cavity as the brush is withdrawn. It is unavoidable, however, that during the cleaning process some of the debris will be pushed by the brush further into the cavity and will become trapped in the blind end of the cavity. As a result of repeated use and cleaning of the handpiece over time, debris trapped in the cavity of the coupling will build up to the point where the shank of the surgical tool cannot be properly maintained in the cavity of the coupling or be properly driven by the output shaft. Another approach to cleaning the cavity of debris involves disassembling the handpiece, which ordinarily must be performed at the manufacturer's facility at considerable inconvenience, time and expense.

An additional drawback to conventional motorized surgical handpieces relates to their inability to effectively seal the interior of the handpiece from foreign substances including contaminants, such as the debris generated by the cutting operation, and cleaning substances. Consequently, the life of the motor in many motorized surgical handpieces is often prematurely shortened due to the exposure to foreign substances such as contaminants and cleaning substances, especially given the need for the handpieces to be sterilized to medical standards after each use. In motorized surgical handpieces where seals are provided on the output shaft, the seals produce friction that undesirably limits the rotational speed of the output shaft and, therefore, the rotational speed of the surgical tool.

Surgical cutting instruments having hollow driven shafts have been proposed, as represented by U.S. Pat. No. 2,144,342 to Morrison, U.S. Pat. No. 3,049,018 to Lusskin et al, U.S. Pat. No. 3,120,845 to Horner, U.S. Pat. No. 4,736,742 to Alexson et al, and U.S. Pat. No. 5,207,697 to Carusillo et al. The Horner, Alexson et al and Carusillo et al patents disclose motorized handpieces, but the handpieces do not incorporate non-contacting seals to seal the motors and the interiors of the handpieces from foreign substances. U.S. Pat. No. 3,082,009 to Whitley et al, U.S. Pat. No. 3,302,951 to Olesen, U.S. Pat. No. 3,804,423 to Booy, U.S. Pat. No. 4,565,378 to Wehfritz et al, U.S. Pat. No. 4,913,447 to Jostlein, U.S. Pat. No. 5,540,447 to Schultz et al, and U.S. Pat. No. 5,794,942 to Vance et al are illustrative of rotating shafts associated with air pressurized or labyrinth seals. In the Whitley et al, Olesen, Booy, Jostlein, Schultz et al and Vance et al patents, the seals are not attached to and do not rotate with the shafts. In the Wehfritz patent, air pressure is used to separate normally contacting sealing surfaces.

In view of the above, there is a need for a motorized surgical handpiece wherein the motor driven output shaft has a through bore defining a portion of a continuous lumen extending entirely through the handpiece to allow for insertion of a bore brush through the lumen for cleaning. The need also exists for a motorized surgical handpiece which has, in addition to the aforementioned continuous lumen, a pair of labyrinth seals including rotor seal components respectively attached to the rotatable output shaft at forward and rearward ends of the motor and stator seal components separated from the rotor seal components by a labyrinthine clearance to which pressurized air can be supplied to force foreign substances away from the motor during use and during cleaning after use.

SUMMARY OF THE INVENTION

The present invention is generally characterized in a motorized surgical handpiece for driving a surgical tool to perform a cutting operation on anatomical tissue at a surgical site. The handpiece comprises a housing enclosed an interior, a motor contained in the interior of the housing, an output shaft driven in rotation by the motor, forward and rearward labyrinth seals associated with the output shaft, and a continuous lumen extending entirely through the handpiece formed in part by a through bore of the output shaft. The output shaft has a forward end portion extending forwardly beyond a front end of the motor and a rearward end portion extending rearwardly beyond a back end of the motor. The forward labyrinth seal comprises a forward labyrinth seal rotor component attached to the forward end portion of the output shaft for rotation therewith and a forward labyrinth seal stator component having an opening therethrough rotatably receiving the forward labyrinth seal rotor component with there being a labyrinthine clearance between the forward labyrinth seal rotor component and the forward labyrinth seal stator component. The rearward labyrinth seal comprises a rearward labyrinth seal rotor component attached to the rearward end portion of the output shaft for rotation therewith and a rearward labyrinth seal stator component having an opening therethrough rotatably receiving the rearward labyrinth seal rotor component with there being a labyrinthine clearance between the rearward labyrinth seal rotor component and the rearward labyrinth seal stator component. The clearances communicate with the interior of the housing and with the environment exterior to the housing, and the clearances prevent contact between the rotor components and their corresponding stator components. Fluid supply passages are provided in the housing for supplying pressurized air to the clearances to flow in a direction away from the interior of the housing and toward the environment exterior to the housing. The pressurized or compressed air is supplied to the clearances during use and during cleaning of the handpiece to avoid the entry of foreign substances into the interior. When the handpiece is not connected with a surgical tool, a bore brush can be inserted into and through the continuous lumen for cleaning. The forward end portion of the output shaft may extend to the exterior of the housing and may have a configuration exterior of the housing for direct driving engagement with the shank of the surgical tool received in the bore of the output shaft. A tool retention device may be provided in the housing for releasable locking engagement with a proximal end portion of the shank which extends into the interior of the housing from the rearward end portion of the output shaft. The housing may support a fluid supply tube associated with a discharge orifice for discharging fluid at the surgical site.

Various objects, benefits and advantages of the present invention will become apparent from the following description of a preferred embodiment taken in conjunction with the accompanying drawings wherein like parts in each of the several figures are identified by the same reference characters.

BRIEF DESCRIPTION OF THE DRAWINGS

FIG. 10 is a broken side view of the surgical tool.

DESCRIPTION OF THE PREFERRED EMBODIMENT

Figure 1:
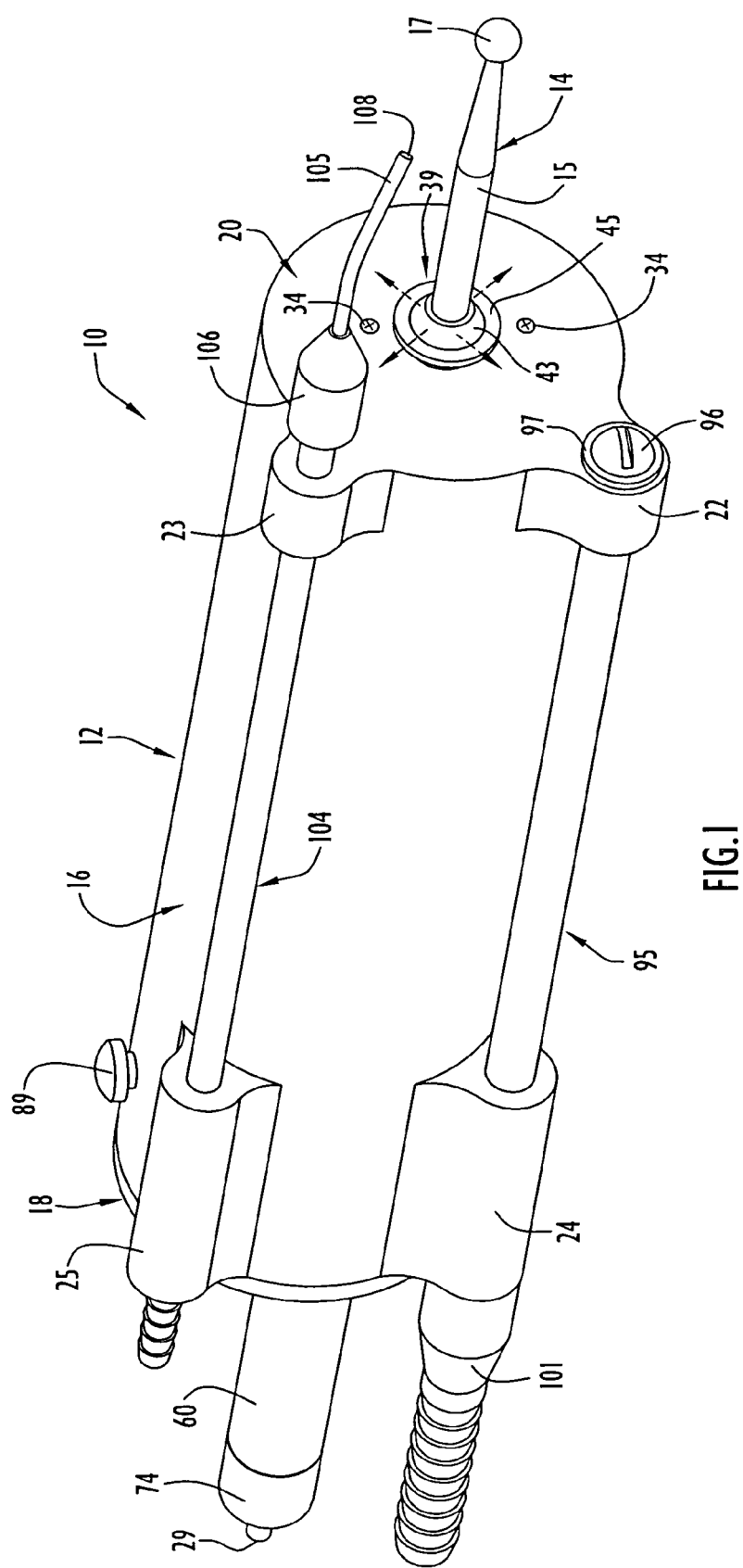
FIG. 1 is a side perspective view of a motorized surgical instrument including a motorized surgical handpiece according to the present invention and a surgical tool coupled with the handpiece.
Figure 2:
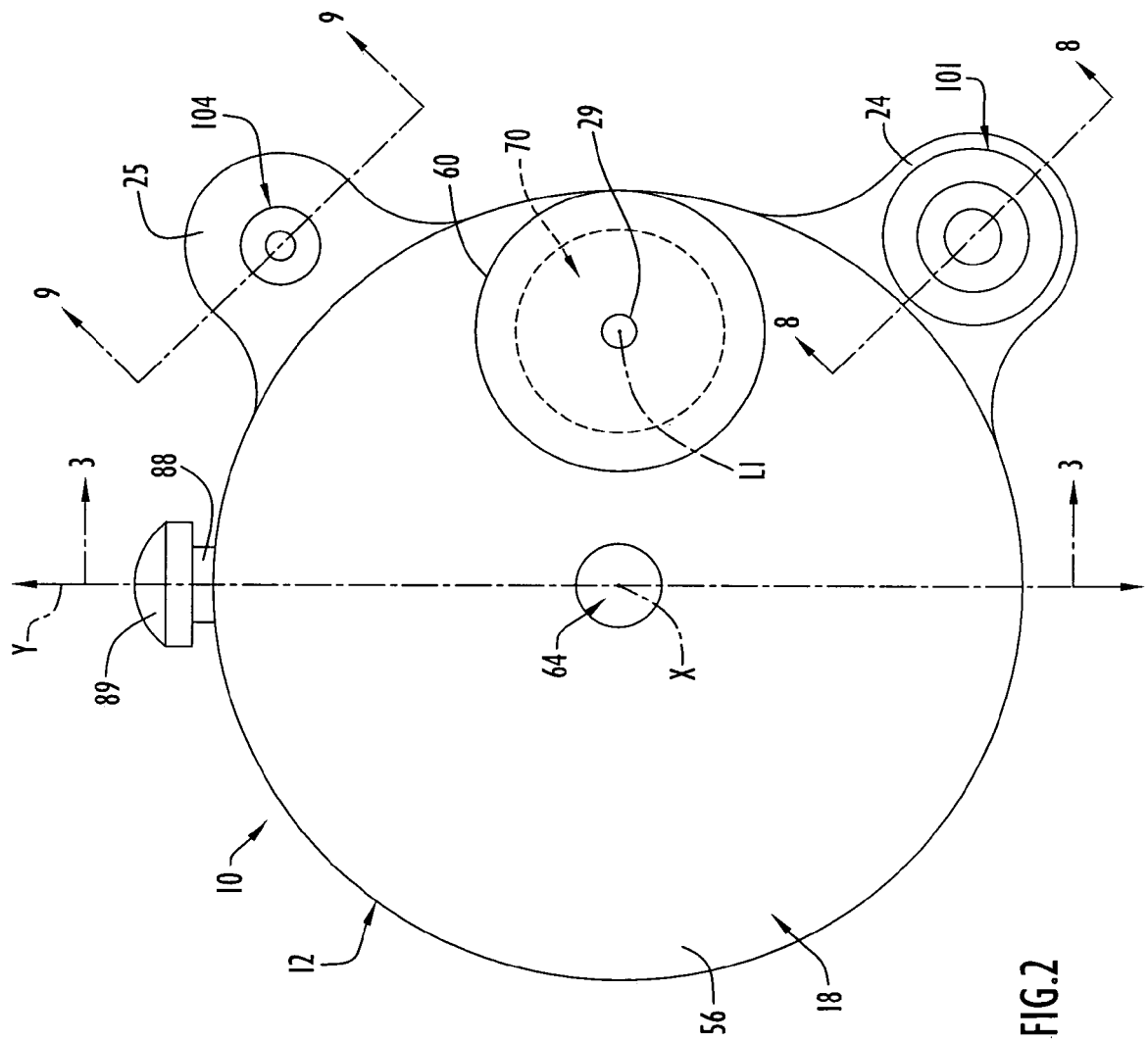
FIG. 2 is a back end view of the motorized surgical instrument and handpiece.
Figure 3:
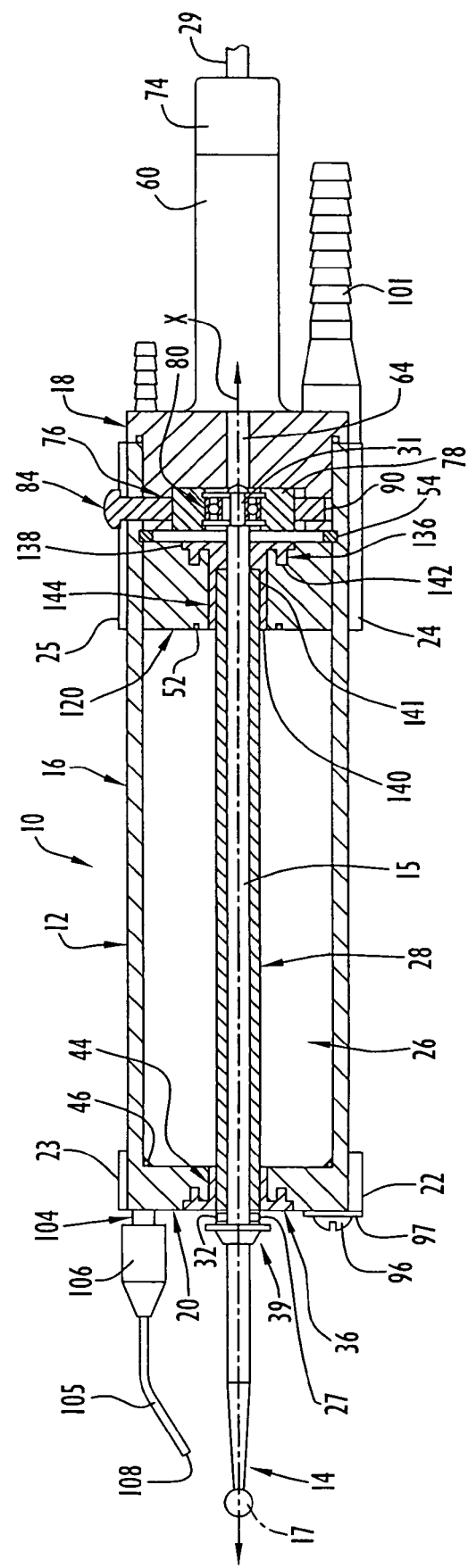
FIG. 3 is a longitudinal side view, partly in section, of the motorized surgical instrument taken along line 3-3 of FIG. 2.

A motorized surgical instrument 10 incorporating a motorized surgical handpiece 12 according to the present invention is depicted in FIGS. 1-3. The motorized surgical instrument 10 comprises the motorized surgical handpiece 12 and a surgical tool 14 removably coupled to the handpiece 12 to be driven in rotation by a motor driven output shaft of the handpiece 12. The handpiece 12, as best shown in FIGS. 1-4, has a housing comprising a body 16 and an end cap 18 mounted on a rearward end of the body 16. The body 16 has a central longitudinal axis X, an interior, a forward end closed by a forward end wall 20, an open rearward end closed by end cap 18 to enclose the interior, a first forward radial extension 22, a first rearward radial extension 24, a second forward radial extension 23 and a second rearward radial extension 25. The body 16 has an external configuration conducive to being grasped by the hand of a user, the body 16 having a cylindrical external configuration with a cylindrical side wall and a planar forward end wall 20 perpendicular to the central longitudinal axis X. The body 16 contains an internal register bore and face in its interior for receiving and locating an electric motor 26 in the interior of the body. The motor 26 has a front end adjacent the forward end wall 20 and has a back end located in the interior of the body 16. The motor 26 drives output shaft 28 of the handpiece in rotation when electrical power is supplied to the motor 26 from an electrical power source. The output shaft 28 has a rearward portion that extends rearwardly beyond the back end of motor 26 to terminate at a rearward shaft end located in the interior of the body 16. Various types and sizes of motors suitable for surgical applications and producing various rotational speeds for the output shaft 28 can be used in the handpiece 12. As an example, the motor 26 can be a brushless DC motor driving a stainless steel output shaft 28 at rotational speeds of up to about 70,000 RPM. However, it should be appreciated that the handpiece of the present invention can incorporate motors capable of higher rotational speeds. An electric power cord 29 on the handpiece 12 can be used to electrically couple the handpiece 12 with the electrical power source, only a portion of the length of power cord 29 being shown in the drawing.

The output shaft 28 is hollow with a through bore 30 extending axially entirely therethrough. The output shaft 28 and its through bore 30 are coaxial with the central longitudinal axis X. The output shaft 28 is disposed in the interior of body 16 with a forward end portion of the output shaft 28 extending forwardly beyond the motor 26 through an opening in forward end wall 20 to terminate at a forward shaft end disposed exteriorly of the body 16. The forward end portion of output shaft 28 at the forward shaft end has a configuration, such as a diametric drive slot 32, for driving engagement with a drive formation, such as a drive pin, on the surgical tool 14 as explained further below. The forward end wall 20 may include holes therethrough aligned with mounting holes in a front end of the motor 26 for receiving screws 34 threadedly engaged in the mounting holes of the motor as illustrated in FIG. 1.

The housing for handpiece 12 is preferably made of a material, such as stainless steel, suitable for use in a surgical environment. The external and internal components of handpiece 12 are designed to withstand repeated sterilization, such as sterilization by autoclaving. The body 16 of the handpiece 12 may be formed integrally unitarily or monolithically as a single component or part, or the body 16 may be formed of multiple components or parts assembled together in any suitable manner to form the body of the handpiece.

Figure 4:
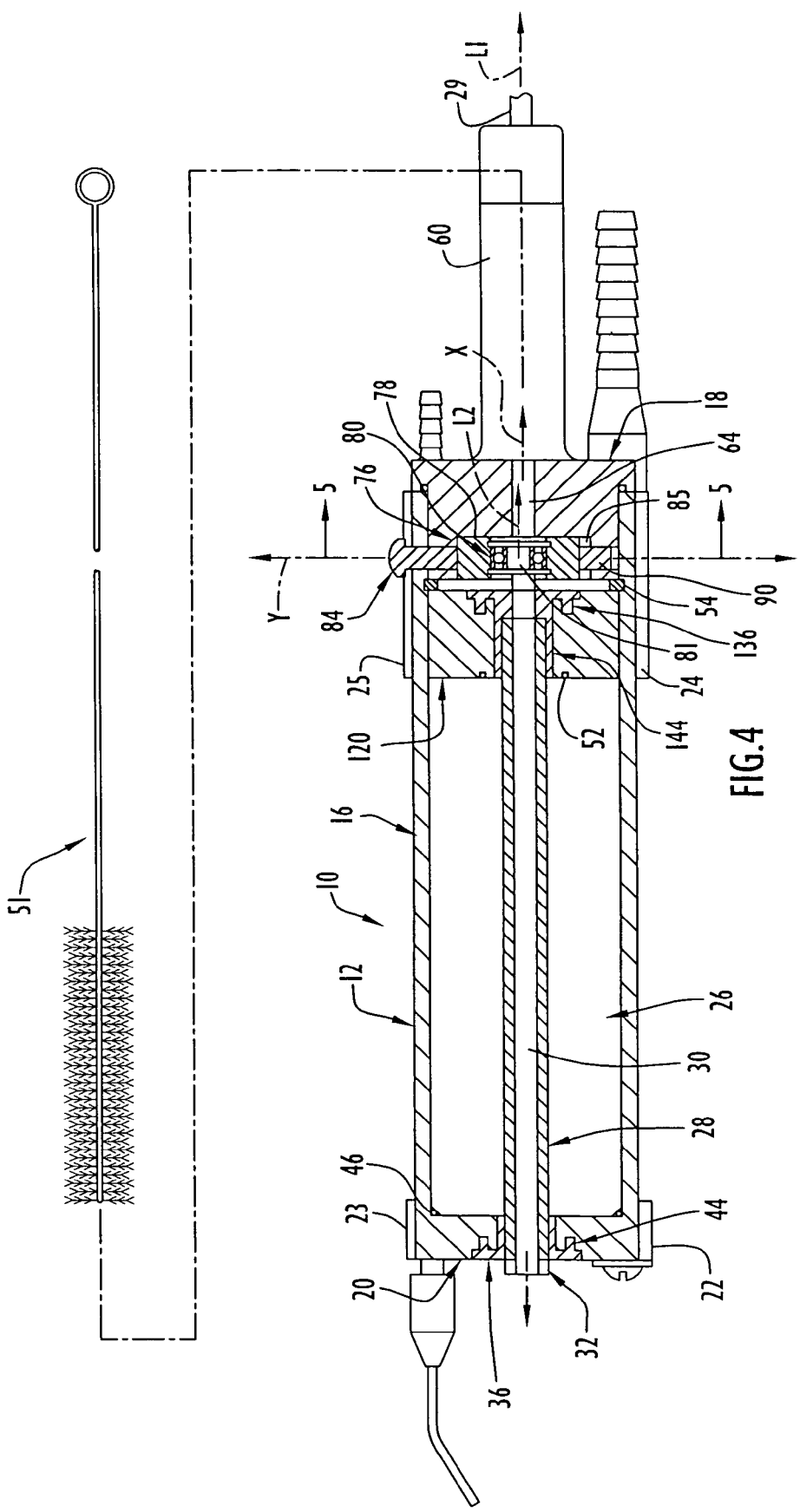
FIG. 4 is a longitudinal side view, partly in section, of the motorized surgical handpiece with the surgical tool removed from the handpiece.
Figure 7:
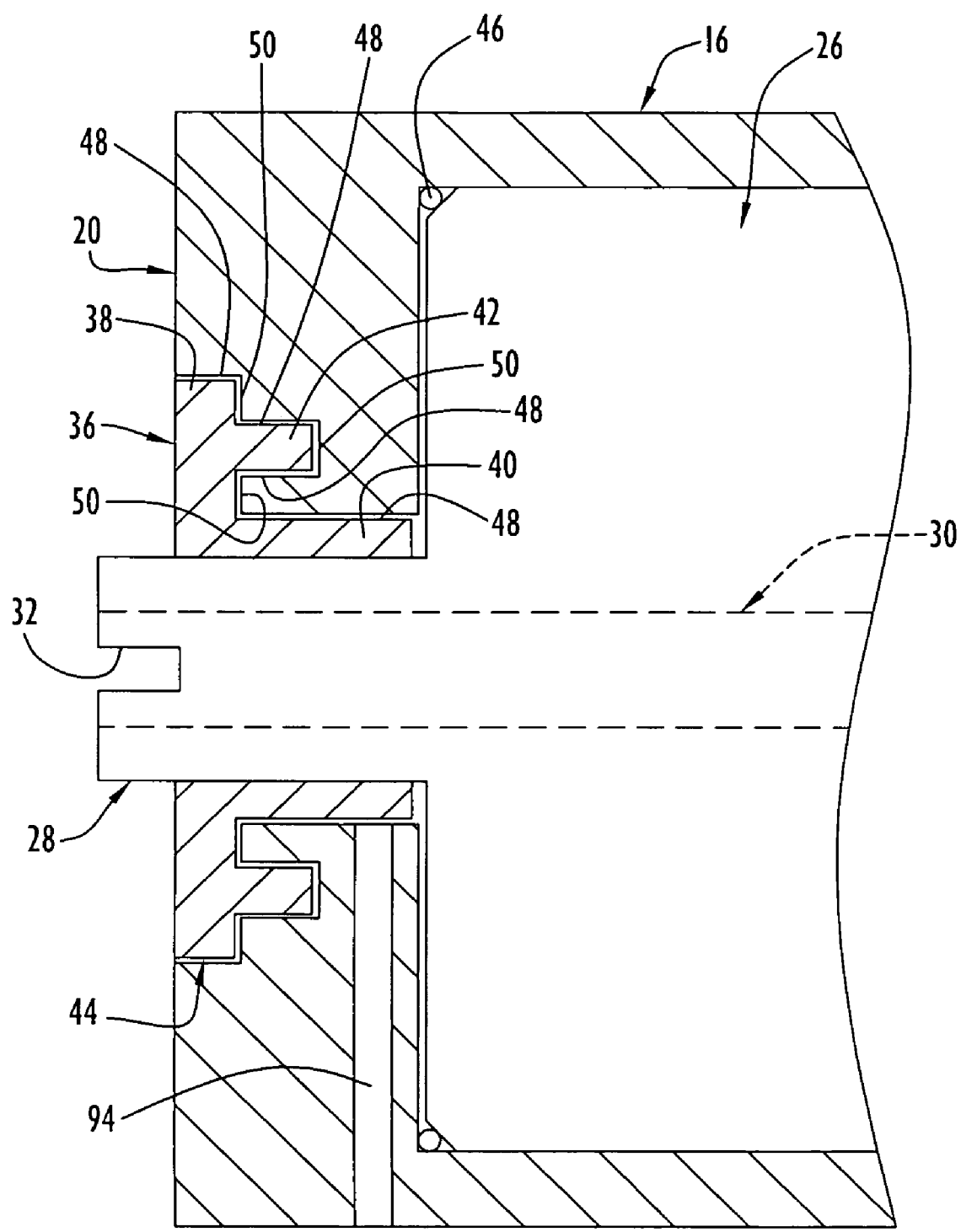
FIG. 7 is a broken longitudinal side view, partly in section, of the motorized surgical handpiece showing a forward labyrinth seal of the handpiece.

As best shown in FIGS. 3, 4 and 7, the handpiece 12 comprises a forward labyrinth seal including a forward labyrinth seal rotor component 36 affixed on the forward end portion of output shaft 28 that extends through the opening of forward end wall 20 and a forward labyrinth seal stator component formed by the forward end wall 20. The forward labyrinth seal rotor component 36 rotates with the output shaft 28 within the opening of the forward labyrinth seal stator component 20, which is stationary and fixed in place. The forward labyrinth seal rotor component 36 has a central passage extending longitudinally therethrough to receive the output shaft 28 therethrough coaxially. The forward labyrinth seal rotor component 36 includes a circular disc 38, a hollow inner cylindrical section 40 extending longitudinally rearwardly from a planar rearward face of the disc 38 in concentric relation therewith, and a hollow outer cylindrical section 42 extending longitudinally rearwardly from the rearward face of the disc 38 in spaced concentric relation around the inner cylindrical section 40. The central passage through the rotor component 36 which receives the output shaft 28 is defined by the hollow interior of the inner cylindrical section 40 and by an aperture through disc 38 continuous with the interior of inner cylindrical section 40. The diametric size of the central passage through the rotor component 36 can be selected to allow the rotor component 36 to be affixed on the output shaft 28 with a press or interference fit. The inner cylindrical section 40 extends longitudinally from the rearward face of disc 38 a greater distance than the outer cylindrical section 42 and is thusly of greater length than the outer cylindrical section 42. The outer diameter of disc 38 is greater than the outer diameter of the outer cylindrical section 42, and the inner diameter of the outer cylindrical section 42 is greater than the outer diameter of the inner cylindrical section 40 to define a stepped profile.

The opening in the forward end wall 20, i.e. the forward labyrinth seal stator component, has a configuration complementary to the external configuration of the forward labyrinth seal rotor component 36 such that the forward labyrinth seal rotor component 36 is rotatably received in the opening of the forward labyrinth seal stator component 20 with there being a small labyrinthine or tortuous gap or clearance 44 between the rotor component 36 and the stator component 20. Accordingly, when the rotor component 36 rotates within the opening of the stator component 20, there is no contact between the rotor component 36 and the stator component 20 which would produce friction and limit rotational speed of the output shaft 28. The rotor component 36 is accommodated in the opening of the stator component 20 such that a planar forward face of the disc 38 is aligned or flush with a planar exterior or forward surface of forward end wall 20 and a rearward end of the inner cylindrical section 40 does not protrude beyond an interior or rearward surface of the forward end wall 20 into the interior of body 16. As shown in FIG. 7, the rearward end of the inner cylindrical section 40 can be disposed a small distance forwardly of the interior or rearward surface of the forward end wall 20. The forward labyrinth seal rotor component 36 is thusly disposed entirely within the opening in the forward labyrinth seal stator component 20 and does not protrude beyond the exterior and interior surfaces of the stator component 20. As shown in FIGS. 3, 4 and 7, a seal 46, such as an o-ring seal, is disposed in the interior of body 16 between the front end of motor 26 and the interior surface of forward end wall 20. The seal 46 can have a diametric size corresponding to the inner diameter of the cylindrical side wall of body 16 so that the seal 46 is located adjacent the interior surface of the cylindrical side wall of body 16.

The clearance 44 establishes communication entirely through the forward end wall 20 between the environment exterior to the handpiece 12 and the interior of the body 16. The clearance 44 may be considered as being composed of cylindrical longitudinal clearance segments 48 and circular radial clearance segments 50 interconnecting the longitudinal clearance segments as depicted in FIG. 7. At each location where the clearance 44 transitions from a longitudinal clearance segment 48 to the next radial clearance segment 50, a sharp bend or change in direction of 90° occurs. The clearance 44 thusly presents an irregular or tortuous path through the forward end wall 20, i.e. the forward labyrinth seal stator component. As explained further below, during use and during cleaning of the handpiece 12, pressurized or compressed air is supplied to the clearance 44 via an air supply passage in forward labyrinth seal stator component 20. The air is supplied to clearance 44 to flow in a direction away from the interior of body 16 toward the environment exterior to handpiece 12. The clearance 44 is of sufficient size and sufficient irregularity or tortuosity to allow the pressurized air to reduce in pressure yet maintain sufficient airflow through the clearance toward the exterior of the handpiece 12 to prevent the entry of foreign substances.

Figure 6:
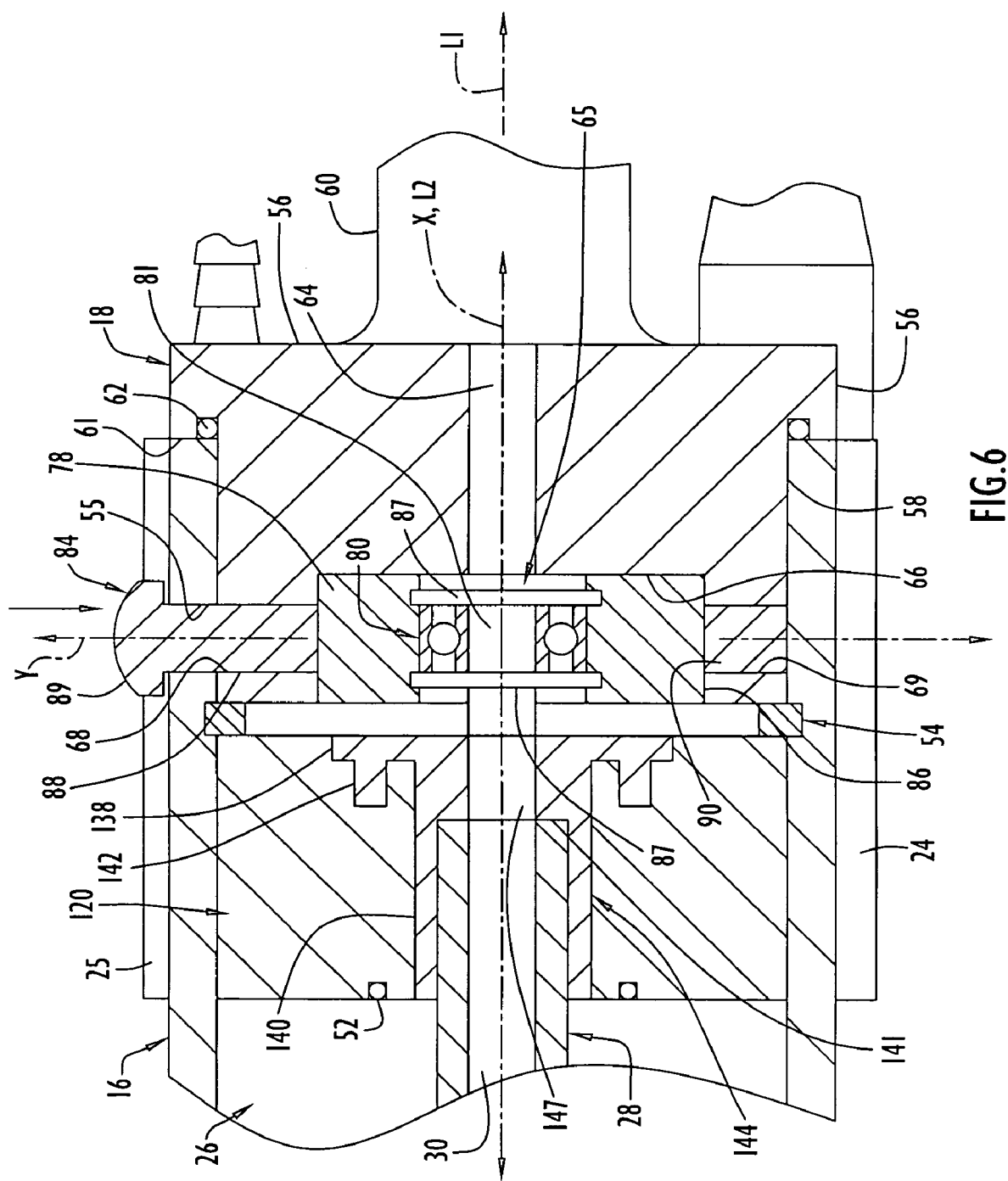
FIG. 6 is a broken longitudinal side view, partly in section, of the motorized surgical handpiece illustrating the tool retention device in a tool releasing or aligned position.

A rearward labyrinth seal rotor component 136 of a rearward labyrinth seal is affixed on the rearward end portion of output shaft 28 adjacent the back end of motor 26. The rearward labyrinth seal comprises the rearward labyrinth seal rotor component 136 and a rearward labyrinth seal stator component 120 located in the interior of body 16 to the rear of the motor 26. The rearward labyrinth seal stator component 120 has an opening extending longitudinally therethrough coaxial with central longitudinal axis X and within which the rearward labyrinth seal rotor component 136 rotates with output shaft 28. As seen in FIGS. 3, 4 and 6, the rearward labyrinth seal rotor component 136 is similar in configuration to the forward labyrinth seal rotor component 36 except that the inner cylindrical section 140 of the rearward labyrinth seal rotor component 136 is greater in length than the inner cylindrical section 40 of the forward labyrinth seal rotor component 36 and has an annular internal shoulder 141 for abutment with the rearward shaft end of output shaft 28, which terminates in the central passage that extends through the rotor component so that the output shaft 28 does not extend entirely through the rotor component 136. Also, the orientation of rearward labyrinth seal rotor component 136 in the opening of stator component 120 is reversed from the orientation of forward labyrinth seal rotor component 36 in the opening of stator component 20. In the case of rearward labyrinth seal rotor component 136, the planar rearward face of its disc 138 is aligned or flush with a planar rearward surface of stator component 120, and the inner cylindrical section 140 and outer cylindrical section 142 extend forwardly from the forward face of the disc 138. The inner cylindrical section 140 terminates at an end surface that does not protrude beyond the forward surface of stator component 120 into the interior of the body 16. As illustrated in FIG. 7 for the rearward surface of stator component 20 and the rearward end surface of inner cylindrical section 40, the forward end surface of inner cylindrical section 140 may be disposed a small distance rearwardly of the forward surface of stator component 120.

Like the forward labyrinth seal rotor component 36, the rearward labyrinth seal rotor component 136 is disposed entirely within the opening of its stator component 120 and does not protrude beyond the forward and rearward surfaces of its stator component 120. The internal shoulder 141 of inner cylindrical section 140 is located intermediate between the forward and rearward surfaces of stator component 120 such that the rearward end portion of output shaft 28 extends part way through the rotor component 136. Because of the internal shoulder 141, the central passage that extends entirely through the rotor component 136 is composed of a larger diameter passage portion forward of the shoulder 141 and a smaller diameter passage portion 147 rearward of the shoulder 141. As seen in FIG. 6, the larger diameter passage portion is preferably of a diametric size to receive the rearward end portion of output shaft 28 therein with a press or interference fit by which the rotor component 136 is affixed on the output shaft 28 and rotates therewith. The smaller diameter passage portion 147 is preferably the same or substantially the same diametric size as the internal through bore 30 of output shaft 28 and is essentially a continuation of the through bore 30. The seal components can be made of any suitable non-corrosive materials such as Delron and stainless steel.

As described above for rotor component 36 and its stator component 20, the opening through the stator component 120 is complementary in configuration to the external configuration of the rotor component 136 to accommodate the rotor component 136 for rotation in the opening of stator component 120 with there being a small labyrinthine gap or clearance 144 between the rotor component 136 and the stator component 120. The clearance 144 presents an irregular or tortuous path entirely through the stator component 120, which is stationary or fixed in place, and prevents contact between the rotor component 136 and the stator component 120. As described further below and as mentioned above for clearance 144, during use and during cleaning of handpiece 12, pressurized or compressed air is supplied to the clearance 144 via an air supply passage in stator component 120. The clearance 144 is of sufficient size and sufficient irregularity or tortuosity to allow the pressurized air to reduce in pressure yet maintain sufficient air flow through the clearance 144 in a direction away from motor 26 to prevent the entry of foreign substances. The back end of motor 26 may have a bell face configuration, and the forward surface of stator component 120 can have a configuration complementary to the configuration of the back end of motor 26. An annular groove is formed in the stator component 120 along its forward surface to receive a seal 52, such as an o-ring seal disposed concentrically around the inner cylindrical section 140 of stator component 120, to establish a seal with the back end of motor 26. An annular groove is formed along the interior surface of the cylindrical side wall of body 16 to be located adjacent the rearward surface of stator component 120, and a retaining ring 54 is mounted in this groove. A front side of the retaining ring 54 abuts the rearward surface of the stator component 120, and a central hole in the retaining ring 54 is coaxially aligned with the bore 30 of output shaft 28 and with the smaller diameter passage portion 147 of the rotor component 136. The retaining ring 54 is preferably a snap ring of thin cross-section and the hole in the retaining ring, together with the passage portion 147, is essentially a continuation of the output shaft bore 30. The retaining ring 54 restricts longitudinal movement of the motor 26 and the stator component 120, and compresses the seal 52 against the back end of the motor 26. The stator component 120 has an aperture formed therein for the passage therethrough of electrical wires from the motor 26, the wires passing through the retaining ring 54 into a rearward extension of end cap 18 as explained further below. A hole 55 is formed through the cylindrical side wall of body 16 rearwardly of the retaining ring 54 for alignment with a radial cavity section of end cap 18 as explained further below.

As best seen in FIGS. 2 and 6, the end cap 18 comprises a rearward end wall 56, a forward extension 58 extending forwardly from the rearward end wall 56 and a rearward extension 60 extending rearwardly from the rearward end wall 56. The forward extension 58 is of cylindrical external configuration with an external diameter smaller than the external diameter of end wall 56. The external diameter of the forward extension 58 corresponds to the inner diameter of the cylindrical side wall of body 16 so that the forward extension 58 is received with a close fit within the open rearward end of body 16. An annular shoulder 61 is defined between a cylindrical outer surface of end wall 56 and the cylindrical outer surface of forward extension 58 for abutment with a rearward end surface of body 16 when a forward end surface of forward extension 58 is in abutment with a back side of retaining ring 54. An annular recess is formed in end cap 18 along shoulder 61 adjacent the cylindrical outer surface of forward extension 58 for receiving a seal 62, such as an o-ring seal, to establish a seal with the rearward end surface of body 16. The cylindrical outer surface of end wall 56 has an external diameter corresponding to the external diameter of the cylindrical side wall of body 16 such that the outer surface of rearward end wall 56 is essentially continuous with the cylindrical outer surface of the body 16. The end cap 18 closes the open rearward end of body 16 and the rearward end wall 56 serves as the rearward end wall for the housing.

Figure 5:
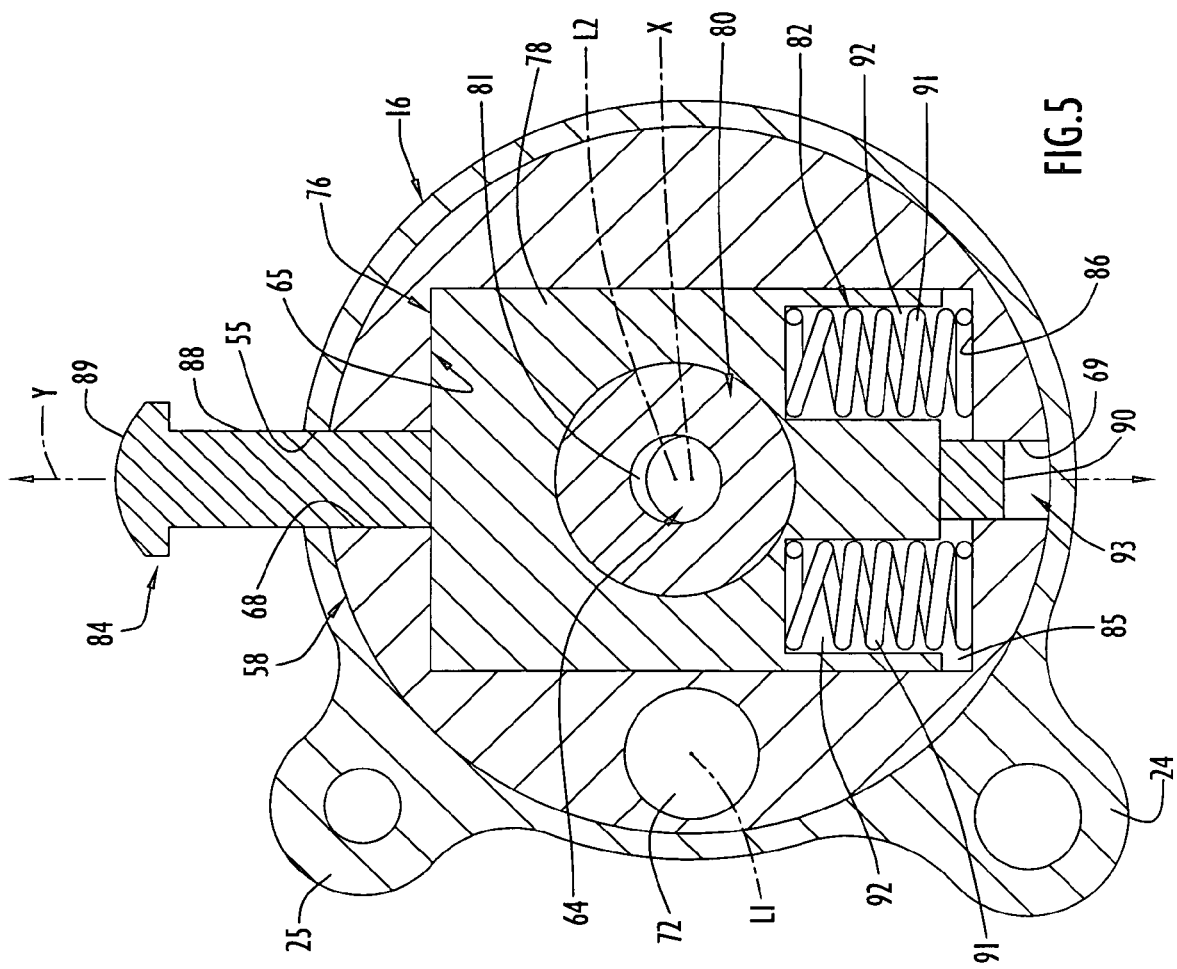
FIG. 5 is a sectional view of the motorized surgical handpiece taken along line 5-5 of FIG. 4 and depicting a tool retention device of the handpiece in a tool engaging or offset position.

The end cap 18 has a passage therethrough coaxial with central longitudinal axis X when the end cap 18 is assembled to the body 16. The passage in end cap 18 is composed of a bore 64 and a window 65 in communication with the bore 64. The bore 64 opens on a back surface of rearward end wall 56 and extends forwardly from the end wall back surface to an internal end wall 66 in end cap 18. The window 65 extends forwardly from the internal end wall 66 to open on the forward end surface of forward extension 58. The passage through the end cap 18 thusly provides communication between the output shaft bore 30 and the environment external to the housing. The bore 64 is preferably of cylindrical configuration with a diameter the same or substantially the same as the diameter of the output shaft bore 30. The window 65 is intersected by radial cavities 68 and 69 formed in the forward extension 58 of the end cap 18 on opposite sides of the window 65. When the end cap 18 is assembled to the body 16, the radial cavities 68, 69 are coaxial with an offset or diametric axis Y of the handpiece that intersects the central longitudinal axis X perpendicularly. The radial cavities 68 and 69, which may be cylindrical, extend entirely through the forward extension 58 and, together with the window 65, provide communication entirely through the forward extension 58 along the diametric axis Y. The window 65 may be rectangular in cross-section as seen in FIG. 5, with a cross-sectional dimension along axis Y that is greater than the diameter of bore 64. The radial cavity 68 is aligned with the hole 55 in body 16 when the end cap 18 is assembled to the body 16 with the forward end surface of forward extension 58 in abutment with the back side of retaining ring 54, the shoulder 61 in abutment with the rearward end surface of body 16, and the bore 64 coaxial with the output shaft bore 30.

The rearward extension 60 extends longitudinally in the rearward direction from the back surface of rearward end wall 56 in laterally or radially offset relation to the central longitudinal axis X and bore 64 as best seen in FIGS. 2 and 6. The rearward extension 60 has a central longitudinal axis L1 parallel to central longitudinal axis X. The central longitudinal axis L1 is radially or laterally spaced from central longitudinal axis X along a radial line perpendicular to central longitudinal axis X and diametric axis Y. The rearward extension 60 is preferably hollow and cylindrical in external configuration with an interior 70, shown in FIG. 2, that communicates with a channel 72, shown in FIG. 5, extending through end wall 56 and forward extension 58 to establish communication through the forward extension 58 and end wall 56 for the electric wires from motor 26 to pass through the retaining ring 54 and into the interior 70 of rearward extension 60. As shown in FIG. 5, the channel 72 is laterally or radially offset or spaced from the window 66 in forward extension 58 and can be coaxial with the central longitudinal axis L1 of rearward extension 60. The interior 70 of rearward extension 60 is closed by a cover 74 at a back end of the rearward extension 60. The cover 74 may be threadedly secured on the back end of the rearward extension 60 via an externally threaded stem of the cover in threaded engagement with an internal thread of the rearward extension 60. The stem of cover 74 threadedly received in the back end of rearward extension 64 can be used to position a wire crimp and nut assembly in the interior 70 to prevent pull out of the motor wires, which are electrically connected with the electrical power cord 29 extending from the cover 74. An end of the power cord 29 not seen in the drawings can be electrically coupled with an external electric power source to supply electrical power to the motor 26 in a conventional manner. The handpiece 12 can be associated with a controller, such as a console, a foot pedal, or a hand switch, for selectively controlling the supply of electric power to the motor 26 to control rotation of the motor driven output shaft 28. The power cord 29 can be designed to connect the handpiece 12 with the controller.

The forward extension 58 of end cap 18 supports a tool retention device 76 in the body 16. As illustrated most clearly in FIGS. 3-6, the tool retention device 76 includes a slide 78 disposed in window 65 for movement therein along diametric or offset axis Y, a bearing assembly mounted in the slide 78 comprising a bearing 80 defining a bearing passage 81 extending therethrough perpendicular to diametric axis Y, a spring mechanism 82 for biasing the slide 78 to an offset or tool engaging position where the bearing passage 81 is normally offset from the bores 30,64, and an operating member 84 disposed exteriorly of the handpiece 12 for selectively moving the slide 78 from the offset position to an aligned or tool releasing position where the bearing passage 81 is coaxial with the bores 30,64. The slide 78 is dimensioned for a close fit in window 65 between internal end wall 66 of forward extension 58 and the back side of retaining ring 54. As seen in FIGS. 4 and 5, the slide 78 has a dimension or size along diametric axis Y that is smaller than the cross-sectional dimension or size of window 65 along axis Y, such that a space 85 is present in the window 65 between the slide 78, when biased by the spring mechanism 82, and an internal side wall 86 of window 65. Slide 78 has an opening therethrough extending in the longitudinal direction of the handpiece 12 and of sufficient size to mount the bearing assembly.

The bearing assembly further includes a pair of bearing snap rings 87 respectively mounted in annular grooves along the interior surface of slide 78 that circumscribes the opening therethrough. The bearing 80 is confined between the bearing snap rings 87 against movement in the longitudinal or axial direction of the handpiece 12. The bearing 80 has an inner bearing surface defining the bearing passage 81 therethrough to receive and support the surgical tool 14 for rotation in the bearing passage 81 as explained further below. The bearing passage 81 has a diametric size the same or substantially the same as the diametric size of the output shaft bore 30. The bearing passage 81 has a central longitudinal axis L2 that intersects the diametric axis Y perpendicularly and extends parallel to central longitudinal axis X when the slide 78 is in the offset position. The bearing passage 81 communicates the output shaft bore 30 with the end cap bore 64. Accordingly, the handpiece 12 has a continuous lumen extending longitudinally entirely therethrough and comprising the output shaft bore 30, the smaller diameter passage portion 147 of rotor component 136, the hole in retaining ring 54, the window 65, the bearing assembly and its bearing passage 81, and the end cap bore 64. Any suitable bearing can be used for the bearing 80 including ball bearings.

The operating member 84 includes a control rod 88 and a button 89. The control rod 88 is attached at one end thereof to slide 78, with the control rod 88 disposed in the radial cavity 68 with a close cross-sectional fit to restrict movement of the slide 78 in the axial or longitudinal direction of the handpiece. The rod 88 extends through the radial cavity 68 and the hole 55 in body 16 to terminate at the button 89 exterior of the handpiece 12. The rod 88 is slidable in the radial cavity 68 and hole 55 along the diametric axis Y. The button 89 is larger in size than the hole 55 in body 16 to maintain the position of the button 89 exterior of the handpiece. A guide element or pin 90 extends from the slide 78 in opposition to the rod 88 and is disposed in the opposite radial cavity 69 for sliding movement along diametric axis Y. The slide 78, the bearing assembly within slide 78, the operating member 84 and the guide pin 90 move along diametric axis Y as a single unit. When the slide 78 is biased by the spring mechanism 82, the guide pin 90 is spaced from the interior surface of the cylindrical side wall of body 16 which is disposed over the radial cavity 69 when the end cap 18 is assembled to the body 16.

FIG. 5 depicts the spring mechanism 82 which biases the slide 78 to be normally disposed in the offset position. The spring mechanism 82 includes a pair of springs 91 respectively disposed in spring compartments 92 formed in slide 78 on opposite sides of central longitudinal axis X and diametric axis Y. The spring compartments 92 are also disposed on opposite sides of guide pin 90, with the spring compartments 92 opening into the space 85 to face the internal side wall 86 which contains the radial cavity 69 that receives the guide pin 90. The springs 91 are respectively mounted in compression between internal side wall 86 and an interior end wall of the corresponding spring compartment 92. The springs 91 exert a biasing force against the slide 78 which causes the slide 78 to be normally displaced in a predetermined offset direction so that the slide 78 is normally disposed in the offset position where the central longitudinal axis L2 of bearing passage 81 is axially offset from the central longitudinal axis X in the offset direction. The spring mechanism 82 is depicted as comprising two springs 91, which are illustrated as coil springs extending lengthwise parallel to the diametric axis Y. It should be appreciated, however, that any suitable number and type of spring can be used in the spring mechanism 82 to bias the slide 78 in a predetermined offset direction so that the slide is normally disposed in the offset position.

When the slide 78 is in the offset position, the button 89 of operating member 84 is elevated or spaced outwardly from the exterior surface of the cylindrical side wall of body 16 in the offset direction along diametric axis Y. The central longitudinal axis L2 of the bearing passage 81 is spaced in the offset direction from the central longitudinal axis X and is parallel to the central longitudinal axis X. The central longitudinal axis L2 of the bearing passage 81 is radially or laterally spaced from the central longitudinal axis X along the diametric axis Y with both the axes X and L2 intersecting the diametric axis Y perpendicularly. The slide 78 is spaced in the offset direction from the internal side wall 86 of window 65 so that the space 85 is presented between the slide 78 and the internal side wall 86. The end of guide pin 90 is spaced in the offset direction from the interior surface of the cylindrical side wall of body 16 so that a space 93 is presented between the end of the guide pin 90 and the interior surface of the cylindrical side wall of body 16. Because the bearing passage 81 is spaced in the offset direction, its bearing surface is offset or inwardly spaced from the inner wall of output shaft bore 30. Accordingly, the bearing surface of the bearing passage 81 presents an obstruction, protrusion or interference in the continuous lumen through the handpiece 12 formed by the output shaft bore 30, the smaller diameter passage portion 147 of stator component 120, the hole in retaining ring 54, the window 65, the bearing assembly and its bearing passage 81, and the end cap bore 64.

By pressing inwardly on button 89 as shown by an arrow in FIG. 6, the slide 78 is movable from the offset or tool engaging position to an aligned, non-offset, or tool releasing position where the central longitudinal axis L2 of bearing passage 81 is coaxial with the central longitudinal axis X so that the bearing surface of bearing passage 81 is aligned with the inner wall of output shaft bore 30 and no longer presents an obstruction, protrusion or interference in the continuous lumen through the handpiece 12. By pushing inwardly on button 89, the control rod 88 is moved inwardly in the radial cavity 68, the slide 78 is moved by the control rod 88 in a direction opposite the offset direction toward the internal side wall 86, and the guide pin 90 is moved by the slide 78 in the radial cavity 69 toward the interior surface of the cylindrical wall of body 16. Inward movement of the operating member 84 to a position where the bearing passage 81 is coaxial with central longitudinal axis X can be limited or controlled by virtue of abutment of the button 89 with the exterior surface of the cylindrical side wall of body 16, abutment of the slide 78 with the internal side wall 86 and/or abutment of the end of guide pin 90 with the interior surface of the cylindrical side wall of body 16.

Figure 8:
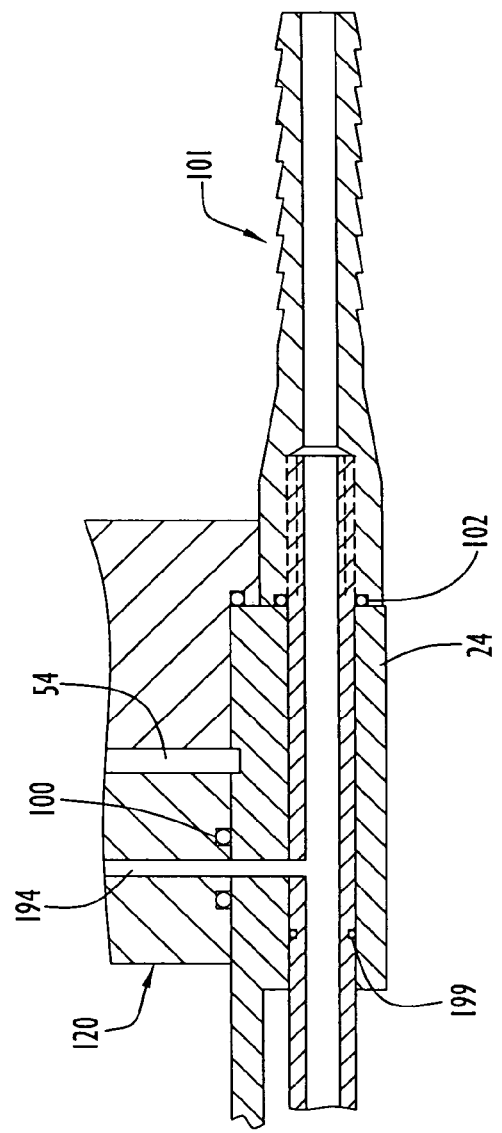
FIG. 8 is a broken longitudinal side view, partly in section, taken along line 8-8 of FIG. 2.
Figure 8:
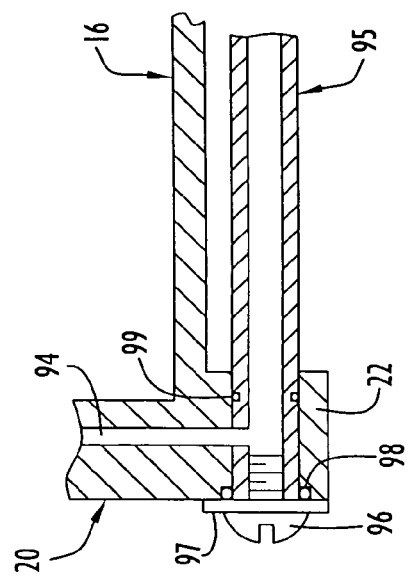

The supply of pressurized or compressed air to the labyrinth clearances 44, 144 can best be understood with reference to FIGS. 7 and 8. As seen in FIG. 7, an air supply passage 94 for the clearance 44 is located within the forward end wall 20, i.e. the forward labyrinth seal stator component, to establish communication between the clearance 44 and an air supply conduit 95 disposed exteriorly of the body 16. The air supply passage 94 communicates with clearance 44 at a location close to the rearward surface of the stator component 20 so that the air supplied to the clearance 44 via the air supply passage 94 flows through the clearance 44 in a direction away from the motor 26 toward the environment external to the handpiece 12. The air supply conduit 95 extends longitudinally alongside the body 16 parallel to the central longitudinal axis X. The air supply conduit 95 extends entirely through a longitudinal passage in first rearward radial extension 24 to a forward end terminating in a longitudinal passage in first forward radial extension 22. The air supply conduit 95 has an internal lumen extending entirely therethrough for the passage of pressurized or compressed air. A hole in the side wall of the air supply conduit 95 located in first forward radial extension 22 establishes communication between the lumen of the air supply conduit and the air supply passage 94. The forward end of air supply conduit 95 may have an internal thread for threaded engagement with the external thread of a screw 96 inserted in the lumen of the air supply conduit 95 via the longitudinal passage in the first forward radial extension 22 to secure the air supply conduit to the body 16. As shown in FIG. 8, the head of screw 96 may bear against the forward surface of first forward radial extension 22 via a washer 97 interposed between the head of the screw and the forward surface of the radial extension 22. The forward surface of radial extension 22 has a recess for accommodating a seal 98, such as an o-ring seal, disposed around the forward end of the air supply conduit 95 with a close fit, with the seal 98 being compressed by the washer 97. A seal 99, such as an o-ring seal, is disposed in a groove formed in the outer surface of the air supply conduit 95 within the longitudinal passage of the first forward radial extension 22 to be located to the rear of the air supply passage 94 and the opening in the wall of air supply conduit 95 that communicates with the air supply passage 94.

As shown in FIG. 8, an air supply passage 194 for the clearance 144 is located within the stator component 120 for the rearward labyrinth seal and establishes communication between the clearance 144 and the lumen of the air supply conduit 95 in a manner similar to that described for air supply passage 94. Like the air supply passage 94, the air supply passage 194 extends from the clearance 144 to a hole in the side wall of air supply conduit 95 located in the passage of the first rearward radial extension 24 to establish communication between the clearance 144 and the lumen of the air supply conduit 95. The air supply passage 194 may communicate with the clearance 144 at a location between the forward and rearward surfaces of the stator component 120 where a substantial portion of the air supplied to the clearance 144 via the air supply passage 194 will flow rearwardly in a direction away from the motor 26 and toward the environment external to the handpiece 12. A seal 199, such as an o-ring seal, is disposed in a groove formed in the outer surface of the air supply conduit 95 within the longitudinal passage of the radial extension 24 to be located in front of the air supply passage 194 and the opening in the side wall of air supply conduit 95 that communicates with the air supply passage 194. Also, a groove is formed in the stator component 120 around the air supply passage 194 adjacent the interior surface of the cylindrical side wall of body 16 to accommodate a seal 100, such as an o-ring seal.

As seen in FIG. 8, the air supply conduit 95 may include an end fitting or connector 101 secured on a rearward end of the air supply conduit 95 which extends rearwardly from the longitudinal passage of the first rearward radial extension 24. The rearward end of the air supply conduit 95 can be externally threaded for threaded engagement with an internal thread of the fitting 101. The fitting 101 is counter-bored to accommodate a seal 102, such as an o-ring seal, disposed around the rearward end of the air supply conduit 95 adjacent a rearward surface of radial extension 24, the seal 102 being compressed when the fitting 101 is threaded onto the rearward end of the air supply conduit 95. The fitting 101 is hollow and has an external barbed configuration at its free end for being coupled with an air supply line or hose to supply compressed or pressurized air from an external air source through the fitting 101 and into the lumen of air supply conduit 95. Of course, it should be appreciated that the air supply conduit 95 and the fitting 101 need not be formed from separate components or parts but, rather, can be formed integrally, unitarily or monolithically.

Figure 9:
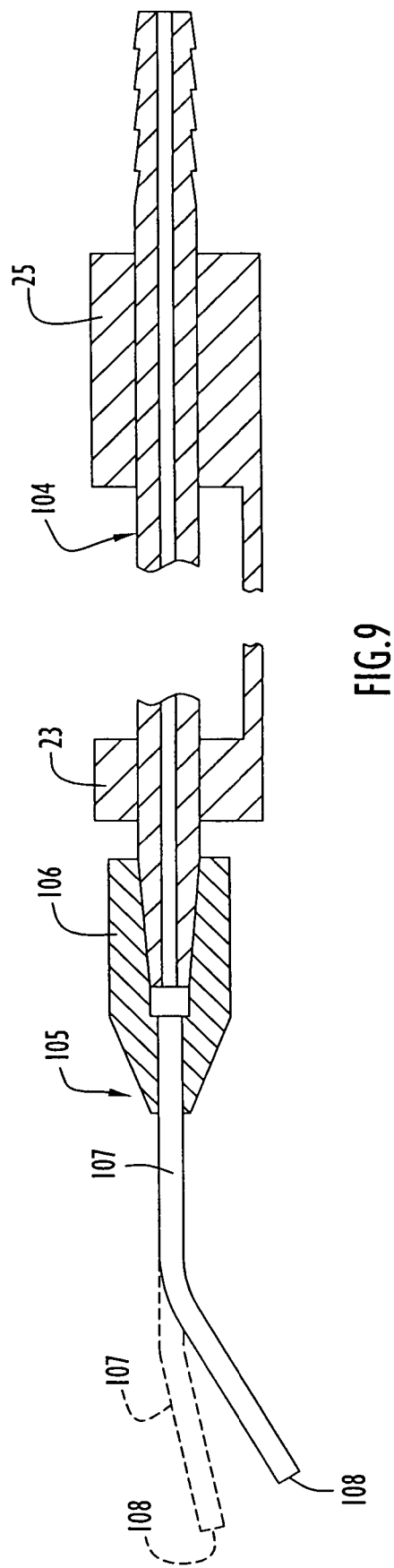
FIG. 9 is a broken longitudinal side view, partly in section, taken along line 9-9 of FIG. 2.

The second forward and rearward radial extensions 23 and 25 of body 16 are used to mount a fluid supply tube 104 on the body 16. As shown in FIGS. 1 and 9, the fluid supply tube 104 extends through longitudinal passages in the second forward and rearward radial extensions 23 and 25 and has a tapered forward end and an externally barbed rearward end for being coupled with an end of a fluid supply hose to supply fluid to fluid supply tube 104 from an external fluid source. The forward end of the fluid supply tube 104 carries a nozzle 105.

The nozzle 105 has a hub 106 secured on the forward end of the fluid supply tube 104 and a nozzle head 107 extending from the hub 106 to an exit orifice 108. The nozzle head 107 is preferably bendable to allow the exit orifice 108 to be positioned to face in any desired direction for the discharge of fluid therefrom. Of course, it should be appreciated that the fluid supply tube 104 and the nozzle 105 can be formed monolithically or integrally unitarily.

The surgical tool 14 is best depicted in FIG. 10 and comprises an elongate shank 15 having a distal end and a proximal end, and a cutter 17 carried on the distal end of the shank. The proximal end of the shank 15 may be rounded or provided with a semi-spherical configuration. The cutter 17 can have various different cutting configurations suitable to perform a cutting operation on anatomical tissue at a surgical site when the cutter 17 is driven in rotation. The type of cutting operation can vary depending on the cutting configuration of the cutter. For example, the cutter 17 can have a drill or bur cutting configuration with a plurality of cutting edges 19 separated by flutes 21 as shown in FIG. 10. In the remainder of the drawings where the cutter 17 is shown, it is depicted without a specific configuration since various different cutting configurations are possible. Also, various different surgical tools can be used interchangeably with the handpiece 12.

The shank 15 has an external diameter to fit closely within the bore 30 of output shaft 28 to maintain proper axial alignment of the surgical tool 14 with the output shaft 28. The shank 15 has a formation 27 for direct engagement with the configuration 32 of output shaft 28. The formation 27 is depicted as a diametric drive pin 27 with ends extending in opposite directions from the outer surface of the shank 15 for reception in the configuration or drive slot 32 to place the output shaft 28 in direct driving engagement with the surgical tool 14 as shown in FIG. 3. The shank 15 is of sufficient length for the cutter 17 to be spaced a sufficient distance in front of the forward end wall 20 to access the anatomical tissue at the surgical site when the drive pin 27 is engaged with drive slot 32. A portion of the shank 15 disposed externally of the handpiece 12 can taper diametrically to the cutter 17 as shown in FIGS. 1, 3 and 10. As shown in FIG. 3, the shank 15 is also of sufficient length for a neck 31 of the shank 15 to be disposed in the bearing passage 81 when the shank 15 is engaged to be driven in rotation by the output shaft 28 via engagement of the drive pin 27 and drive slot 32. The neck 31 is formed by a reduced diameter section of shank 15 between a pair of longitudinally spaced forward and rearward shoulders 33 and 35. The neck 31 has an external diameter to be rotatably received within the bearing passage 81 with the forward and rearward shoulders 33 and 35 in interfering relation with the bearing assembly to prevent withdrawal of the surgical tool 14 from the handpiece 12 when the slide 78 is in the offset position as shown in FIG. 3. In particular, the bearing surface of the bearing 80 is in interfering relation with the shoulders 33, 35 and blocks the shank 15 from being withdrawn from the bearing passage 81. When the slide 78 is moved to the axially aligned position by depressing the button 89 as explained above and shown in FIG. 6, the bearing assembly is no longer in interfering relation with the shoulders 33, 35 so that the surgical tool 14 can be inserted in or withdrawn from the handpiece 12.

As shown in FIGS. 1, 3 and 10, a diverter or slinger 39 is disposed on the shank 15 to be located close to the forward shaft end of output shaft 28 when the drive pin 27 is engaged in the drive slot 32. The diverter 39 comprises a tapered nose 43 having a narrower forward end and a wider rearward end, a base 45 attached to the wider rearward end of the nose 43, a central longitudinal axis aligned with the center of nose 43 and base 45, and a through passage coaxial with the central longitudinal axis. The nose 43 can have a frustoconical configuration, and the base 45 can have a circular configuration. The through passage of the diverter 39 has a diametric size to receive the shank 15 coaxially therethrough with a close fit, the base 45 being perpendicular to the central longitudinal axis of the surgical tool 14. The diverter 39 is attached to the shank 15 and rotates with the surgical tool 14 when the surgical tool is driven in rotation by the output shaft 28. Preferably, the diverter 39 is attached to the shank 15 so that the base 45 is located close to the forward shaft end of output shaft 28 without interfering with engagement of the drive pin 27 in drive slot 32, with the nose 43 of the diverter tapering in the direction of the cutter 17.

When the surgical tool 14 is not assembled with the handpiece 12, the continuous lumen extends entirely through the handpiece coaxial with the central longitudinal axis X and comprising the bore 30 of output shaft 28, the smaller diameter passage portion 147 in stator component 120, the hole in retaining ring 54, the window 65, the holes in snap rings 87, the bearing passage 81, and the end cap bore 64. The tool retention device 76 is normally in the offset position with the central longitudinal axis L2 of the bearing passage 81 offset from the central longitudinal axis X of the lumen through the handpiece 12 such that the bearing assembly protrudes inwardly into the handpiece lumen and presents an obstruction, protrusion or constriction in the handpiece lumen. In order to assemble the surgical tool 14 to the handpiece 12, the shank 15 of the surgical tool 14 is inserted, proximal end first, in the bore 30 via the open forward end of output shaft 28. The button 89 is depressed and is maintained in the depressed position to move slide 78 to the aligned position where the central longitudinal axis L2 of bearing passage 81 is coaxial with the central longitudinal axis X. With the slide 78 maintained in the aligned position, the shank 15 is pushed rearwardly in the lumen of the handpiece so that the drive pin 27 enters the drive slot 32 and the neck 31 is received in the bearing passage 81. Abutment of the drive pin 27 with the end of the drive slot 32 and/or abutment of the proximal end of shank 15 with the internal wall 66 can serve as a stop or abutment limiting insertion of the shank 15 to the proper distance. Once the neck 31 is received in the bearing passage 81, release of the button 89 allows the slide 78 to return automatically to its offset position due to the biasing force of the spring mechanism 82 and as permitted due to the smaller external diameter of the neck 31 being disposed in the bearing passage. When the tool retention device 76 has returned to its offset position, the bearing assembly is in interfering or obstructing relation with the shoulders 33 and 35 of the shank 15 and the shank 15 is thusly confined against longitudinal movement. Interference between the bearing assembly and the rearward shoulder 35 prevents withdrawal of the surgical tool 14 from the handpiece 12 such that the surgical tool 14 is locked to the handpiece 12 with the output shaft 28 in driving engagement with the tool 14. It should be appreciated that movement of the slide 78 to the aligned position to allow insertion of the shank 15 through the bearing passage 81 could be accomplished without manually depressing the button 89 in that the proximal end of shank 15 can itself move the bearing assembly into axial alignment with the central longitudinal axis X as it is forcefully pushed rearwardly into the lumen of the handpiece 12.

When the surgical tool 14 is assembled and locked to the handpiece 12, the shank 15 is directly coupled with the output shaft 28 to be driven in rotation by the output shaft without the need for a separate coupling on the output shaft. The drive pin 27 and drive slot 32 which operate to establish driving engagement between the output shaft 28 and the surgical tool 14 are disposed exteriorly of the handpiece 12 and are exposed for cleaning after removal of the surgical tool 14 from the handpiece 12. The shank 15 extends entirely through the output shaft 28 and motor 26 and extends entirely through the rearward labyrinth seal and bearing assembly.

During use, electrical power is supplied to motor 26 from an electrical power source via power cord 29. The output shaft 28 is driven in rotation by the motor 26, and the surgical tool 14 is rotated by the output shaft 28. In order to perform a cutting operation on anatomical tissue at a surgical site, the cutter 17 is positioned adjacent the anatomical tissue so that the anatomical tissue is cut as a result of rotation of the cutter 17. During the cutting operation, irrigating fluid or any other type of fluid desired to augment the surgical procedure may be introduced at the surgical site via the fluid supply tube 104. The fluid, from an external fluid source, is supplied to the fluid supply tube 104 via an appropriate hose connected to the barbed end of the fluid supply tube for discharge of the fluid at the surgical site through the exit orifice 108. By bending the nozzle head 107, the exit orifice 108 can be positioned to face in any desired direction for the discharge of fluid.

During the cutting operation, compressed or pressurized air is supplied to the labyrinth clearances 44 and 144 through the air supply conduit 95 and the air supply passages 94,194. The air is supplied from an external air source via an air supply line connected to the end fitting 101, and the air flows from the air supply conduit 95 into the air supply passages 94,194 and then into the clearances 44,144. The air introduced into the clearances 44, 144 flows in opposite directions away from the motor 26 and toward the environment exterior to the handpiece. Because of the airflow in clearances 44, 144 away from the motor 26, contaminants are prevented from entering the clearances 44,144 and the interior of the body 16. Since the forward end of the handpiece 12 is likely to be exposed to the most contaminants generated as a result of the surgical procedure, the air flow from clearance 44 toward the exterior environment ensures that the forward end wall 20 of the handpiece 12 is not breached by contaminants. The rotor components 36,136 of the forward and rearward labyrinth seals do not contact their stator components 20,120 as the rotor components rotate with the output shaft 28, thereby avoiding the creation of friction which would otherwise limit the rotational speed of the surgical tool 14. Accordingly, the surgical tool 14 can be rotated by the output shaft 28 at very high rotational speeds. During the surgical procedure, it can be expected that contaminants will flow down the shank 15 toward the forward end of the handpiece 12, and the diverter 39 which rotates with the surgical tool 14 operates to divert the flow of contaminants in a direction radial to the surgical tool as shown by arrows in FIG. 1. In particular, during rotation of the surgical tool 14, centrifugal force will redirect the natural spiral axial flow of contaminants in the radial direction. In addition, the diverter 39 presents a physical barrier that serves to shield the forward ends of the output shaft and handpiece from contaminants.

In addition to compressed air being supplied to the clearances 44,144 during operation and use of the handpiece 12, compressed air is also supplied to the clearances 44,144 as part of the cleaning process for the handpiece 12. Cleaning of the handpiece 12 after use involves first withdrawing the surgical tool 14 from the handpiece 12 by depressing the button 89 to move the slide 78 to the aligned position axially align the bearing passage 81 with the central longitudinal axis X and pulling the surgical tool 14 in a forward direction from the handpiece 12. Once the surgical tool 14 is withdrawn from the handpiece 12, the continuous lumen in the handpiece 12 can be thoroughly cleaned by inserting a bristled end of a bore brush 51, shown in FIG. 4, into and entirely through the lumen. The bristled end of the bore brush 51 can be inserted into the handpiece lumen from either the output shaft bore 30 or the end cap bore 64. When the bristled end of the bore brush 51 is pushed entirely through the lumen of the handpiece 12, any contaminants or debris in the lumen will be pushed entirely through and out of the lumen. In addition, compressed air is supplied to the clearances 44,144 via the air supply conduit 95 so that any contaminants in the handpiece 12 are pushed away from the motor 26 and the interior of body 16 and are forced to exit the handpiece due to the clearances 44 and 144 being in communication with the environment external to the handpiece. Whenever air is supplied to the clearances 44, 144, it is not necessary for the motor 26 and output shaft 28 to be rotating. As part of the cleaning procedure, the handpiece 12 will also typically be sterilized, such as by autoclave sterilization, to medical standards.

When compressed or pressurized air is supplied to the clearances 44,144, the flow of supplied air in the clearances 44,144 in opposite directions away from the interior of the handpiece 12 provides resistance to the flow of fluidic or fluid-carried foreign substances in the clearances 44,144 in directions opposed to the flow of the supplied air. The flow of supplied air in clearance 44 in the forward direction resists a rearward flow of fluidic or fluid-carried foreign substances in clearance 44. Conversely, the flow of supplied air in the clearance 144 in the rearward direction resists a forward flow of fluidic or fluid-carried foreign substances in clearance 144. Fluidic or fluid-carried foreign substances which have sufficient velocity to penetrate one or more of the right angle bends of the clearances 44,144 will encounter increasing resistance to flow further into the labyrinth seals due to the increasing pressure of the supplied air flowing outwardly in the clearances. Accordingly, fluidic or fluid-carried foreign substances that may have entered the clearances 44,144 from the exterior are prevented from flowing entirely through the clearances 44,144 into the interior of the handpiece 12.

Inasmuch as the present invention is subject to various modifications, variations and changes in detail, it is intended that the description of the preferred embodiments provided above be taken as illustrative only and not be taken in a limiting sense.

What is claimed is:

1. A motorized surgical handpiece for driving a surgical tool to perform a cutting operation on anatomical tissue at a surgical site, said handpiece comprising a housing enclosing an interior;

a motor disposed in said interior and having a front end and a back end;

an output shaft disposed in said interior for being rotatably driven by said motor, said output shaft having a forward end portion extending forwardly beyond said front end of said motor, a rearward end portion extending rearwardly beyond said back end of said motor, and a longitudinal bore extending entirely through said output shaft for receiving a shank of a surgical tool to be driven in rotation by said output shaft;

a forward labyrinth seal including a forward labyrinth seal rotor component attached to said forward end portion of said output shaft for rotation with said output shaft and a forward labyrinth seal stator component having an opening therethrough rotatably receiving said forward labyrinth seal rotor component with there being a labyrinthine clearance between said forward labyrinth seal rotor component and said forward labyrinth seal stator component, said clearance of said forward labyrinth seal being in communication with said interior and with the environment exterior of said housing;

a rearward labyrinth seal including a rearward labyrinth seal rotor component attached to said rearward end portion of said output shaft for rotation with said output shaft, and a rearward labyrinth seal stator component having an opening therethrough rotatably receiving said rearward labyrinth seal rotor component with there being a labyrinthine clearance between said rearward labyrinth seal rotor component and said rearward labyrinth seal stator component, said clearance of said rearward labyrinth seal being in communication with said interior and with the environment exterior of said housing;

means for supplying pressurized air to said clearances to flow in a direction away from said motor and toward the environment exterior of said housing; and a continuous lumen extending longitudinally entirely through said housing and formed in part by said bore of said output shaft.

2. The motorized surgical handpiece recited in claim 1 wherein said housing includes a forward end wall serving as said forward labyrinth seal stator component.

3. The motorized surgical handpiece recited in claim 1 wherein said forward end portion of said output shaft extends entirely through said forward labyrinth seal rotor component and said opening of said forward labyrinth seal stator component to the environment exterior of said housing, said forward end portion having a configuration exterior of said housing for direct driving engagement with the shank of the surgical tool.

4. The motorized surgical handpiece recited in claim 1 wherein said means for supplying pressurized air includes forward and rearward air supply passages in said housing for respectively introducing pressurized air into said clearances of said forward and rearward labyrinth seals and an air supply conduit connecting said forward and rearward air supply passages to receive pressurized air from said air supply conduit.

5. The motorized surgical handpiece recited in claim 4 wherein said air supply conduit extends along the exterior of said housing.

6. The motorized surgical handpiece recited in claim 1 and further including a fluid supply tube extending along the exterior of said housing to an exit orifice selectively positionable to discharge fluid at the surgical site.

7. The motorized surgical handpiece recited in claim 3 and further comprising a surgical tool having a shank with a proximal end for being disposed in said lumen and a distal end carrying a cutter, said shank being of sufficient length to extend forwardly from said forward end portion of said output shaft to position said cutter to cut anatomical tissue at the surgical site, said shank having a formation between its distal and proximal ends for engaging said configuration of said forward end portion of said output shaft in direct driving engagement.

8. The motorized surgical handpiece recited in claim 7 wherein said configuration includes a slot in said output shaft and said formation includes a drive pin on said shank for being received in said slot.

9. The motorized surgical handpiece recited in claim 7 and further including a diverter on said shank disposed forwardly of said forward end portion of said output shaft for diverting away from said housing the flow of contaminants along said shank generated as a result of the cutting operation.

10. A motorized surgical handpiece for driving a surgical tool to perform a cutting operation on anatomical tissue at a surgical site, said handpiece comprising a housing enclosing an interior and including a forward end wall having an opening therethrough and a rearward end wall having a passage therethrough in longitudinal alignment with said opening;

a motor disposed in said interior between said forward end wall and said rearward end wall;

an output shaft disposed in said interior for being driven in rotation by said motor, said output shaft having a longitudinal bore extending entirely therethrough for receiving a shank of a surgical tool to be rotatably driven by said output shaft to cut anatomical tissue at a surgical site, a forward end portion extending through said opening to a forward shaft end disposed exteriorly of said housing, and a rearward end portion extending to a rearward shaft end disposed in said interior, said bore being in longitudinal alignment with said passage;

a forward labyrinth seal comprising a forward labyrinth seal stator component formed by said forward end wall, a forward labyrinth seal rotor component attached on said forward end portion of said output shaft for rotation in said opening with there being a labyrinthine clearance between said forward labyrinth seal rotor component and said forward labyrinth seal stator component;

a rearward labyrinth seal comprising a rearward labyrinth seal stator component disposed in said interior and having an opening therethrough longitudinally aligned with said passage, a rearward labyrinth seal rotor component attached on said rearward end portion of said output shaft for rotation in said opening of said rearward labyrinth seal stator component with there being a labyrinthine clearance between said rearward labyrinth seal rotor component and said rearward labyrinth seal stator component;

a forward air supply passage in said forward labyrinth seal stator component for supplying pressurized air to said clearance of said forward labyrinth seal to flow in a direction away from said front end of said motor;

a rearward air supply passage in said rearward labyrinth seal stator component for supplying pressurized air to said clearance of said rearward labyrinth seal to flow in a direction away from said back end of said motor;

a tool retention device in said housing to the rear of said rearward labyrinth seal for releasably lockingly engaging the shank of the surgical tool; and a continuous lumen extending longitudinally through said housing, said lumen comprising said bore and said passage through said rearward end wall.

11. The motorized surgical handpiece recited in claim 10 wherein said continuous lumen has a central longitudinal axis, said tool retention device comprises a slide supported in said housing for sliding movement along an offset axis perpendicular to said central longitudinal axis, a bearing carried by said slide having a bearing passage for receiving the shank of the surgical tool therethrough and forming a part of said continuous lumen, a spring mechanism for biasing said slide to an offset position along said offset axis where said bearing presents a protrusion in said continuous lumen, and an operating member disposed externally of said housing for moving said slide along said offset axis from said offset position to an aligned position where said bearing does not protrude into said continuous lumen.

12. The motorized surgical handpiece recited in claim 11 and further comprising a surgical tool having a shank with a proximal end for being disposed in said lumen and a distal end carrying a cutter for performing a cutting operation on anatomical tissue when said shank is rotated by said output shaft, said shank having a neck of reduced cross-section for being received in said bearing passage when said slide is in said offset position, said shank having a shoulder that is blocked by said obstruction when said slide is in said offset position to prevent withdrawal of said surgical tool from said handpiece and is not blocked when said slide is in said aligned position to permit withdrawal of said surgical tool from said handpiece.

13. The motorized surgical handpiece recited in claim 10 wherein said operating member comprises a push button and said tool retention device further comprises a control rod connecting said button to said slide.

14. The motorized surgical handpiece recited in claim 13 wherein said tool retention device further comprises a guide element extending from said slide into a cavity in said housing, said guide element being slidable in said cavity as said slide is moved from said offset position to said aligned position.

15. A motorized surgical handpiece for driving a surgical tool to perform a cutting operation on anatomical tissue at a surgical site, said handpiece comprising a housing comprising a body having a central longitudinal axis, an interior, a forward end closed by a forward end wall, and an open rearward end, and an end cap secured to said rearward end to enclose said interior, said end cap having a rearward end wall and a forward extension extending forwardly from said rearward end wall into said interior, said forward end wall having an opening therethrough coaxial with said central longitudinal axis establishing communication between said interior and the environment exterior to said housing, said end cap having an opening therethrough establishing communication between said interior and the environment exterior to said housing, said opening through said end cap including a bore extending from the environment exterior to said housing through said rearward end wall into said forward extension coaxial with said central longitudinal axis and a window extending from said bore to said interior;

a motor disposed in said interior and having a front end and a back end, said front end being adjacent said forward end wall;

an output shaft in said interior coaxial with said central longitudinal axis for being rotatably driven by said motor, said output shaft having an internal surface defining a through bore through said output shaft coaxial with said central longitudinal axis for receiving a shank of a surgical tool therethrough with a close fit, a forward end portion extending forwardly beyond said front end of said motor through said opening in said forward end wall to a forward shaft end located exteriorly of said housing, a rearward end portion extending rearwardly beyond said back end of said motor to a rearward shaft end located in said interior, said forward end portion having a configuration adjacent said forward shaft end for direct driving engagement with the shank of the surgical tool by which the surgical tool is rotatably driven by said output shaft to perform a cutting operation on anatomical tissue at a surgical site;

a forward labyrinth seal comprising a forward labyrinth seal stator component formed by said forward end wall, a forward labyrinth seal rotor component disposed on said forward end portion of said output shaft for rotation with said output shaft in said opening in said forward end wall with there being a labyrinthine clearance between said forward labyrinth seal rotor component and said forward labyrinth seal stator component, said forward labyrinth seal rotor component having a through passage receiving said forward end portion to extend coaxially entirely through said through passage, said clearance being in communication with said interior and with the environment exterior to said housing;

a rearward labyrinth seal comprising a rearward labyrinth seal stator component disposed in said interior adjacent said back end of said motor, said rearward labyrinth seal stator component having an opening therethrough coaxial with said central longitudinal axis, and a rearward labyrinth seal rotor component disposed on said rearward end portion of said output shaft for rotation with said output shaft in said opening of said rearward labyrinth seal stator component with there being a labyrinthine clearance between said rearward labyrinth seal rotor component and said rearward labyrinth seal stator component, said rearward labyrinth seal rotor component having a through passage receiving said rearward end portion to extend coaxially into said through passage of said rearward labyrinth seal rotor component, said clearance of said rearward labyrinth seal being in communication with said opening through said end cap;

an air supply conduit supported to extend exteriorly along said housing for receiving pressurized air from a pressurized air source;

a forward air supply passage in said forward labyrinth seal stator component extending from said clearance of said forward labyrinth seal to said air supply conduit to supply pressurized air from said air supply conduit to said clearance of said forward labyrinth seal during the cutting operation and during cleaning of said handpiece to prevent the entry of foreign substances into said interior from the environment exterior to said handpiece;

a rearward air supply passage in said rearward labyrinth seal stator component extending from said clearance of said rearward labyrinth seal to said air supply conduit to supply pressurized air from said air supply conduit to said clearance of said rearward labyrinth seal during the cutting operation and during cleaning of said handpiece to prevent the entry of foreign substances into said interior from the environment exterior to said handpiece;

a tool retention device comprising a slide mounted for sliding movement in said window along a diametric axis perpendicular to said central longitudinal axis, a bearing assembly carried by said slide including a bearing having an internal bearing surface defining a bearing passage through said bearing in communication with said through bore of said output shaft and said bore of said end cap for receiving the shank of the surgical tool therethrough, a spring mechanism biasing said slide in said window in an offset direction along said diametric axis where said internal bearing surface is inwardly offset from said internal surface of said output shaft in said offset direction to prevent longitudinal movement of the shank of the surgical tool and thereby lock the surgical tool to said handpiece, and an operating member disposed exteriorly of said housing for moving said slide along said diametric axis in a direction opposite said offset direction to align said internal bearing surface with said internal surface of said output shaft to permit longitudinal movement of the shank of the surgical tool and thereby release the surgical tool for removal from said handpiece; and a continuous lumen through said housing comprising said through bore of said output shaft, said bearing passage and said bore of said end cap, said lumen providing communication entirely through said housing when the surgical tool is removed from said handpiece for insertion of a brush entirely through said lumen for cleaning.

16. The motorized surgical handpiece recited in claim 15 wherein said bearing assembly further comprises a pair of bearing snap rings and said bearing is confined longitudinally between said snap rings.

17. The motorized surgical handpiece recited in claim 15 and further including a retention ring mounted in said interior, said rearward labyrinth seal stator component being confined longitudinally between said retention ring and said back end of said motor.

18. The motorized surgical handpiece recited in claim 15 wherein said end cap further comprises a rearward extension extending longitudinally rearwardly from said rearward end wall, said rearward extension having a central longitudinal axis parallel to said central longitudinal axis of said body and being connected with a power cord for supplying power to said motor from an external power source.

19. The motorized surgical handpiece recited in claim 15 and further including a fluid supply tube supported to extend exteriorly along said housing for receiving fluid from a fluid source, said fluid supply tube having a forward end associated with a bendable fluid nozzle for discharging the fluid in a selected direction.

20. The motorized surgical handpiece recited in claim 15 and further including a surgical tool having a shank for being disposed in said lumen with a close fit, said shank having a proximal end for being disposed adjacent said bore in said end cap and a distal end carrying a cutter to be disposed externally of said housing to cut anatomical tissue at the surgical site when said shank is rotatably driven by said output shaft, said shank having a formation for engaging said configuration of said forward end portion of said output shaft in direct driving engagement, said shank having a neck between a pair of raised shoulders, said neck being disposed in said bearing passage with said internal bearing surface being in interfering relation with said shoulders when said slide is in said offset position and being removed from interfering relation with said shoulders when said slide is moved to said aligned position.

* * * * *